(12) United States Patent
Anthony et al.

(10) Patent No.: US 7,385,221 B1
(45) Date of Patent: Jun. 10, 2008

(54) SILYLETHYNYLATED HETEROACENES AND ELECTRONIC DEVICES MADE THEREWITH

(75) Inventors: John E. Anthony, Lexington, KY (US); Marcia M. Payne, Lexington, KY (US); Susan A. Odom, Atlanta, GA (US); Sean Richard Parkin, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 195 days.

(21) Appl. No.: 11/075,144

(22) Filed: Mar. 8, 2005

(51) Int. Cl.
*C07D 327/00* (2006.01)
*C07D 305/00* (2006.01)
*C07F 7/02* (2006.01)

(52) U.S. Cl. .................. 257/40; 548/406; 549/4; 549/214; 257/E51.05; 257/E51.046

(58) Field of Classification Search ................ 548/406; 549/4, 214; 257/40, E51.046, E51.047, E51.049, 257/E51.05; 438/99
See application file for complete search history.

(56) References Cited

U.S. PATENT DOCUMENTS

| | | |
|---|---|---|
| 5,936,259 A | 8/1999 | Katz et al. |
| 6,184,540 B1 | 2/2001 | Chmii et al. |
| 6,509,110 B1 | 1/2003 | Salbeck et al. |
| 6,608,323 B2 | 8/2003 | Marks et al. |
| 6,626,566 B2 | 9/2003 | Holmes et al. |
| 6,690,029 B1 | 2/2004 | Anthony et al. |
| 6,806,374 B2 | 10/2004 | Heeney et al. |
| 6,818,260 B2 | 11/2004 | Farrand et al. |
| 2005/0277776 A1* | 12/2005 | Liu et al. .................. 549/59 |
| 2006/0046092 A1* | 3/2006 | Towns et al. ............... 428/690 |

FOREIGN PATENT DOCUMENTS

WO   WO 2005055248 A2 *   6/2005

OTHER PUBLICATIONS

Sakamoto, Y., Suzuki, T., Kobayashi, M., Gao, Y., Fukau, Y., Inoue, Y., Sato, F. and Tokito, S. "Perfluoropentacene: High-Performance p-n Junctions and Complementary Circuits with Pentacene." J. AM. CHEM. SOC. vol. 126 (2004); pp. 8138-8140.*

Payne, Marcia M. et al., Organic field-effect transistors from solution-deposited functionalized acenes with mobilities as high as 1 cm2 / Vs; J. Am. Chem. Soc.; vol. 127 (2005) pp. 4986-4987.

Marcia M. Payne et al., Stable, Crystalline Acenedithiophenes with up to Seven Linearly-Fused Rings Organic Letters, vol. 6 (2004), pp. 3325-3328.

Laquindanum, Joyce G. et al., Synthesis, Morphology, and Field-Effect Mobility of Anthradithiophenes, J. Am. Chem. Soc. 1998, 120, pp. 664-672.

Kwon, O. et al., Characterization of the molecular parameters determining charge transport in anthradithiophene J. Chem. Phys., vol. 120, No. 17, May 1, 2004, 8186-8194.

* cited by examiner

*Primary Examiner*—Bradley W. Baumeister
*Assistant Examiner*—Matthew W Such
(74) *Attorney, Agent, or Firm*—King & Schickli, PLLC (57) ABSTRACT

Novel silylethynylated heteroacenes and electronic devices made with those compounds are disclosed.

14 Claims, 2 Drawing Sheets

SILYLETHYNYLATED HETEROACENES AND ELECTRONIC DEVICES MADE THEREWITH

This invention was made with support from the Office of Naval Research and by the Defense Advanced Research Projects Agency under Grant No. N00014-02-1-0033. The government may have certain rights in this invention.

TECHNICAL FIELD

The present invention relates generally to the field of organic semiconductors and, more particularly, to silylethynylated heteroacenes as well as to electronic devices made with these compounds.

BACKGROUND OF THE INVENTION

Display technology is expected to become a dominant sector of high-tech industry in the future. It is also expected that the flat panel display technology will be revolutionized by the use of organic semiconductors that will allow manufacture of cheap, flexible, lightweight, fully portable flat panel displays with no apparent limits to their size. It is predicted that due to the lower manufacturing cost, organic semiconductor based displays will eventually gain dominance over amorphous silicon based counterparts and the respective market share will grow to $1.6 billion by 2007. To realize these goals, however, significant breakthroughs will have to take place in the area of organic semiconductor material and device processing.

Interest in organic thin film transistors (OTFTs) for possible use in displays, sensors and other large area electronic applications has been increasing rapidly. Best reported organic thin film transistor (OTFT) device performance rivals or exceeds that of hydrogenated amorphous silicon devices, and low OTFT process temperatures allow fabrication on a range of surfaces including cloth, paper or lower temperature polymeric substrates.

Organic semiconductors for use in OTFTs can be broadly divided into two groups as high and low mobility materials. High mobility materials have mobility >0.1 cm$^2$/V-s, usefully large carrier energy bandwidth (>0.1 eV) and weak or sometimes absent temperature activation of mobility. To date, most high mobility organic semiconductors have been small molecule materials (with pentacene the most notable example) and most have been deposited by vacuum sublimation or from a solution precursor with a high-temperature (>150° C.) conversion step. Low mobility materials have mobility from about $10^{-5}$-$10^{-1}$ cm$^2$/V-s, typically transport carriers by hopping, and have strong temperature activation of mobility. Most polymeric organic semiconductors fall into this group and many have the potential advantage that they can be deposited from solution.

To date, there have been few reports of low-temperature solution processed organic semiconductors with high mobility. In addition, even for low mobility materials, current solution deposition techniques have not demonstrated material structure, thickness and property control comparable to vacuum deposition techniques. The present invention relates to new organic semiconductor compounds with relatively low OTFT process temperatures and relatively high mobility.

SUMMARY OF THE INVENTION

The present invention relates to novel silylethynylated heteroacenes (anthra(diheterocycles), tetra(diheterocycles) and penta(diheterocycles) compounds) as well as to transistors and photovoltaic apparatus made from those compounds. The novel compounds comprise the following formula:

(A₁)

(A₂)

(B₁)

(B₂)

DETAILED DESCRIPTION OF THE INVENTION

The novel compounds of the present invention may be broadly described as silylethynylated heteroacenes. The compounds have the following structural formulae:

(A₁)

(A₂)

(B₁)

(B₂)

(C₁)

(C₂)

wherein R=an alkyl having $C_1$-$C_8$, perfluoroalkyl having $C_1$-$C_8$, aryl, alkoxy or trialkylsilyl, $R^1$=hydrogen, alkyl having $C_1$-$C_8$, aryl, perfluoroalkyl having $C_1$-$C_8$, alkoxy, halogen and x=—O, —S, —Se or —NH.

In accordance with yet another aspect of the present invention a transistor is constructed from the novel compounds of the present invention. The transistor comprises a gate electrode, a semiconductor constructed from the novel compound of the present invention, an insulator between the gate electrode and the semiconductor, a source electrode and a drain electrode.

In accordance with yet another aspect of the present invention, a photovoltaic apparatus is provided. That photovoltaic apparatus comprises a transparent anode, a semiconductor constructed from a novel compound of the present invention, an n-type material and a cathode.

BRIEF DESCRIPTION OF THE DRAWING FIGURES

The accompanying drawing incorporated in and forming a part of the specification, illustrates several aspects of the present invention and together with the description serves to explain certain principles of the invention. In the drawing.

Reference will now be made in detail to the present preferred embodiments of the invention as illustrated in the accompanying drawing figures.

The silylethynylated heteroacenes are prepared as a mixture of isomers.

Formulae A₁ and A₂ represent the two isomers of anthra (diheterocylces). Formulae B₁ and B₂ represent the two isomers of tetra (diheterocyles). Formulae C₁ and C₂ represent the two isomers of penta (diheterocyles). The novel compounds of the present invention include both the mixture of the isomers of Formulae A₁, A₂; B₁, B₂; or C₁, C₂ and the pure isomers A₁, A₂, B₁, B₂, C₁, or C₂.

The isomers A₁, A₂, B₁, B₂, C₁, or C₂ may be purified from the mixture of isomers of Formulae A₁, A₂; B₁, B₂; or C₁, C₂ by methods known to those skilled in the art including but not limited to high-performance liquid chromatography (HPLC).

The novel compounds of the present invention are prepared by a relatively simple and straightforward method. Specifically, the silylethynylated heteroacenes are easily made by the addition of an alkynyllithium to the corresponding acenequinone, followed by reductive workup with either HI or tin (II) chloride:

This type of reaction is well-described in:

Miller, G. P.; Mack, J.; Briggs, J. *Org. Lett.* 2000, 2, 3983.

Anthony, J. E.; Eaton, D. L.; Parkin, S. R. *Org. Lett.* 2002, 4, 15.

Anthony, J. E.; Brooks, J. S.; Eaton, D. L.; Parkin, S. *J. Am. Chem. Soc.* 2001, 123, 9482.

Payne, M. M.; Odom, S. A.; Parkin, S. R.; Anthony, J. E. *Org. Lett.* 2004 6, 3325.

The acenequinone is very easily prepared by a 4-fold aldol condensation between a dialdehyde and commercially-available 1,4-cyclohexanedione:

This condensation is well-described in:

De la Cruz, P.; Martin, N.; Miguel, F.; Seoane, C.; Albert, A.; Cano, H.; Gonzalez, A.; Pingarron, J. M. *J. Org. Chem.* 1992, 57, 6192.

The "R" group of these dialdehydes is typically installed by the following sequence:

-continued

This procedure is described for thiophene dialdehyde in detail in:
Laquindanum, J. G.; Katz, H. E.; Lovinger, A. J. *J. Am. Chem. Soc.* 1998, 120, 664.

Thus the "base unit" for all of these materials is the heterocyclic dialdehyde. Many of these are known in the literature, and some are even commercially available:

Thiophene 2,3-dialdehyde: Commercially available from Aldrich and Acros chemical
Furan 2,3-dialdehyde: Prepared as in Zaluski, M. C.; Robba, M.; Bonhomme, M. *Bull. Chim. Soc. Fr.* 1970, 4, 1445.
Selenophene 2,3-dialdehyde: Prepared as in Paulmier, C.; Morel, J.; Pastour, P.; Semard, D. *Bull. Chim. Soc. Fr.* 1969, 7, 2511.
Thiazole dialdehyde: Prepared as in Robba, M.; Le Guen, Y. *Bull Chim. Soc. Fr.* 1969, 11, 4026.
Imidazole dialdehyde: Prepared as in Kolks, G.; Frihart, C. R.; Coughlin, P. K.; Lippard, S. J. *Inorg. Chem.* 1981, 20, 2933

Other heterocyclic dialdehydes can be prepared by the same methods outlined for the synthesis of the furan and selenophene compounds.

The following synthesis and examples are prepared to further illustrate the invention, but it is not to be considered as limited thereto.

EXAMPLE 1

5,11-Bis(triethylsilylethynyl)anthra [2,3-b:6,7-b'] dithiophene and 5,11-Bis(triethylsilylethynyl)anthra [2,3-b:7,6-b'] dithiophene. To an oven-dried 250-mL round-bottom flask equipped with a stir bar and cooled under $N_2$ was added hexanes (20 mL) and 0.38 mL of triethylsilyl acetylene (2.0 mmol), followed by the dropwise addition of 0.73 mL of n-BuLi (1.8 mmol, 2.46 M solution in hexanes). This mixture was stirred for 1 h, then hexanes (80 mL) and anthradithiophenequinone (prepared by method described in De la Cruz, P. et al. *J. Org. Chem.* 1992, 57, 6192.) (0.16 g, 0.34 mmol) were added. The mixture was heated at 60° C. overnight, then quenched with 0.5 mL of water. $SnCl_2.2H_2O$ (0.50 g, 2.2 mmol) in 10% aq. HCl (1 mL) was added and the mixture was stirred for 2 h at 60° C. The solution was dried over $MgSO_4$, then loaded onto a thick pad of silica. The silica was rinsed with hexanes (500 mL), then the product was eluted using hexanes:DCM (5:1). Removal of solvent yielded 0.18 g (0.31 mmol, 91%) of a reddish powder. Recrystallization from hexanes yielded thick dark-red plates. Recrystallized 3× from hexanes. Yield: 91%. MP: 151° C. $^1$H-NMR (400 MHz, $CDCl_3$) δ=9.18 (s, 2H), 9.13 (s, 2H), 7.57 (d, J=5.6 Hz, 2H, syn isomer), 7.57 (d, J=5.2 Hz, 2H, anti isomer), 7.47 (d, J=5.6 Hz, 2H), 1.27 (tt, J=8.0 Hz, 1.6 Hz, 18H), 0.94 (q, J=8.0 Hz, 12H). $^{13}$C-NMR (400 MHz, $CDCl_3$) δ=140.27, 140.18, 139.82, 139.68, 133.70, 130.11 (2C), 130.01 (2C), 129.92 (2C), 129.81, 129.17, 123.95, 121.50, 121.44, 120.20, 118.05, 117.69, 8.04 (2C), 7.82, 4.93 (2C), 4.50. Anal. calcd % C: 72.02, % H: 6.75. Found % C: 71.68, % H: 6.75.

For preparation of systems with alternative "R" groups, a different acetylene would be substituted for triethylsilyl acetylene in the above preparation. For preparation of systems where "R'" is different from "H" the requisite precursor quinones can be prepared as in (Laquindanum, J. G. et al., *J. Am. Chem. Soc.* 1998, 120, 664.)

EXAMPLE 2

Tetra[2,3-b:8,9-b'] dithiophene-5,13-dione and Tetra[2,3-b:9,8-b']dithiophene-5,13-dione. A 1:2 mixture of 2,3-thiophenedicarboxaldehyde (0.85 g, 6.07 mmol) and benzo[1,2-b]thiophene-4,5-dicarboxaldehyde (1.66 g, 8.70 mmol) was dissolved in THF (200 mL) in a 500-mL round-bottom flask with a stir bar, then 1,4-cyclohexanedione (0.83 g, 7.40 mmol) was added and the solution was stirred until uniform. After the addition of 15% KOH (2 mL), precipitate began to form immediately, and vigorous stirring was continued overnight. The solution was filtered to yield 3.87 g of a light brown powder made up of insoluble quinones which were used directly in the next step: MS (70 eV, EI) m/z 370 (100%, M+).

5,13-Bis(tris(trimethylsilyl)silylethynyl)tetra [2,3-b:8,9-b'] dithiophene and 5,13-Bis(tris(trimethylsilyl)silylethynyl)tetra[2,3-b:9,8-b']dithiophene. To an oven-dried 500-mL round-bottom flask cooled under $N_2$ and equipped with a stir bar was added hexanes (150 mL) and tris((trimethylsilyl) silyl acetylene (14 g, 51.1 mmol). n-BuLi.(19.5 mL, 47,9 mmol, 2.6 M in hexanes) was added dropwise and the mixture was stirred for 2 hr. The above quinone mixture (3.87 g) was added and stirring was continued overnight, followed by the addition of anhydrous THF (20 mL) and additional stirring for 2 d. Water (2 mL) and a solution of $SnCl_2.H_2O$ (10.0 g, 44 mmol) in 10% HCl (20 mL) was added and the solution was stirred for 2 hr. DCM (100 mL) was then added and the organic layer was separated, dried over $MgSO_4$, and rinsed through a thin pad of silica (DCM). Solvent was concentrated to a volume of 10 mL, then diluted with hexanes (200 mL), and rinsed onto a thick pad of silica. The silica was rinsed with hexanes (600 mL), then hexanes:DCM (1:1) to elute the product mixture, and solvent was removed from this second fraction. Using column chromatography (hexanes:ethyl acetate (9:1)), 0.82 g of the desired tetradithiophene were isolated. The tetradithiophene was recrystallized from acetone to yield dark-blue needles. $^1$H-NMR (400 MHz, $CDCl_3$) δ=9.53 (s, 1H), 9.45 (s, 1H), 9.16 (s, 1H), 9.13 (s, 1H), 8.53 (s, 1H), 8.49 (s, 1H), 7.54 (d, J=5.6 Hz, 1H), 7.50 (d, J=6.2 Hz, 1H), 7.41 (s, 1H), 7.40 (s, 1H), 1.08 (s, 54H). $^{13}$C-NMR (400 MHz, $CDCl^3$) δ=140.49, 140.46, 140.20, 140.19, 139.92, 139.86, 138.98, 138.90, 130.27, 129.74, 129.61, 126.84, 125.35, 124.02, 123.72, 122.34, 122.29, 121.64, 121.04, 120.99, 120.29, 107.05, 106.72, 105.64, 104.85, 104.76, 11.5. UV-VIS (DCM): $\lambda_{abs}$ (ε): 244 (18700), 300 (32400), 328 (61800), 372 (6940), 392 (5610), 465 (2110),528 (1340), 555 (1340), 599 (2810), 653 (4960). IR (KBr) $\upsilon_{max}$ ($cm^{-1}$): 2956 (m), 2945 (m), 2860 (s), 2129 (m), 1460 (m), 1400 (m), 1366 (s), 1061 (m), 997 (w), 882 (s), 752 (s), 720 (vs), 661 (s), 586 (m).

EXAMPLE 3

Penta[2,3-b:9,10-b']dithiophene-6,14-dione and Penta[2,3-b:10,9-b']dithiophene-6,14-dione. In a 500-mL round-bottom flask equipped with a stir bar, benzo[1,2-b]thiophene-4,5-dicarboxaldehyde (2.35 g, 12.4 mmol) was dissolved in THF (200 mL). 1,4-Cyclohexanedione (0.70 g, 6.2 mmol) was added and stirred until the solution was uniform, then 15% KOH (2 mL) was added. Vigorous stirring was continued overnight, then the solution was filtered and rinsed with ether (20 mL) and DCM (20 mL). The brown solid was heated to reflux in DMF (400 mL) for 2 hr, then cooled and filtered to yield 1.6 g (3.8 mmol) of the desired quinone as a light brown insoluble powder. MS (70 eV, EI) m/z 420 (42%, M$^+$).

6,14-Bis(tri(t-butyl)silylethynyl)-penta [2,3-b:9,10-b'] dithiophene and 6,14-Bis(tri(t-butyl)silylethynyl)-penta [2,3-b:10,9-b']dithiophene (6b). To an oven-dried 250-mL round-bottom flask equipped with a stir bar and cooled under N$_2$ was added anhydrous THF (40 mL) and tri(t-butyl) silyl acetylene (3.59 g, 16.0 mmol). n-BuLi (5.7 mL, 14 mmol, 2.6 M in hexanes) was added dropwise and the solution was stirred for 1 hr, then the abovementioned quinone (1.6 g, 3.8 mmol) was added. After stirring for 24 hr, additional anhydrous THF (40 mL) was added and stirring was continued for 3 days. Water (2 mL) and a solution of SnCl$_2$.H$_2$O (1.0 g, 4.4 mmol) in 10% HCl (2 mL) was added and the solution was stirred for 2 hr. DCM (200 mL) was added and the organic layer was separated, dried over MgSO$_4$, and rinsed through a thin pad of silica (DCM). Solvent was concentrated to a volume of 10 mL then diluted with hexanes (200 mL). This solution was poured onto a thick pad of silica and rinsed with hexanes (500 mL), then hexanes:DCM (1:1) to elute the product. Removal of solvent yielded 0.44 g (0.53 mmol, 14%) of product as a sparingly-soluble green powder. Recrystallization from toluene, then from CS$_2$ yielded 6b as slender dark green needles. $^1$H-NMR (400 MHz, CDCl$_3$) δ=9.49 (s, 2H), 9.41 (s, 2H), 8.41 (s, 2H), 8.38 (s, 2H), 7.46 (d, J=5.6 Hz, 2H), 7.36 (s, J=5.6 Hz, 2H), 1.50 (s, 54H). $^{13}$C-NMR (400 MHz, CS$^2$/C$_6$D$_6$) δ=140.52, 138.91, 130.98, 130.86, 130.67, 130.55, 129.57, 128.92, 128.88, 128.78, 128.75, 128.26, 127.96, 127.94, 127.59, 126.11, 124.08, 122.94, 121.61, 109.10, 106.70, 97.94, 31.12, 30.81, 28.89, 22.73. UV-VIS (DCM): $\lambda_{abs}$ (ϵ): 277 (42500), 342 (69500), 373 (6350), 398 (2770), 416 (2740), 441 (2220), 475 (1730), 577 (145), 623 (474), 690 (1170), 762 (2600). IR (KBr) $\upsilon_{max}$ (cm$^{-1}$): (cmol): 3400 (w), 2972 (m), 2935 (m), 2859 (5), 2133 (5), 1648 (w), 1385 (s), 1115 (m), 1032 (w), 890 (s), 820 (s), 748 (s), 619 (s). Anal calcd for C$_{54}$H$_{66}$S$_2$Si$_2$.H$_2$O % C: 75.99, % H: 8.03. Found % C: 75.61, % H: 7.93. MS (70 eV, EI) m/z 834 (100%, M$^+$), 777 (63%, M$^+$-C$_4$H$_9$). MP: 268° C. (dec.).

The compounds of the present invention demonstrate remarkable physical and electronic properties. The silyl acetylene unit substituted on the inner aromatic ring serves two important purposes. First it lends solubility to the molecule, allowing processing by simple, solution-based methods. Secondly and perhaps more importantly, this functional group causes the molecules to self-assemble into π-stacked arrays that are critical to improved device performance. More specifically, this molecular arrangement leads to improved conductivity, reduced band gap and field effect transistors (FETs) devices with a hole mobility of 0.001 to 1.0 cm$^2$/Vs.

Figure 1A:
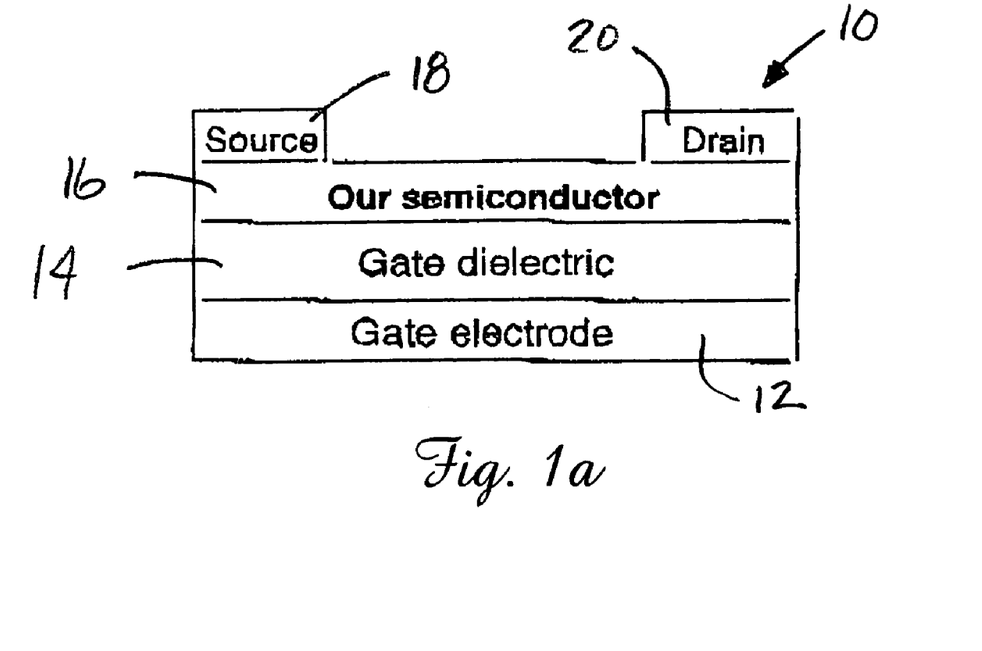
FIGS. 1a and 1b are schematical illustrations of two possible embodiments for the field-effect transistor of the present invention.

A number of useful electronic devices may be constructed from the novel compounds of the present invention. As illustrated in FIG. 1a a field effect transistor (FET) 10 is comprised of a gate electrode 12 of a type known in the art, an insulator or gate dielectric 14 also of a type known in the art and a semiconductor 16 in the form of a thin layer or film of the compounds of the present invention. In addition, the FET 10 includes a conductive source electrode 18 and a drain electrode 20 both operatively connected to the semiconductor 16.

The insulator 14 may, for example, be a dielectric or metal oxide or even an insulating polymer like poly(methylmethacrylate). The conducting source and drain electrodes 18, 20 may be metals known in the art to be useful as electrodes, heavily doped semiconductors such as silicon or even a conducting polymer.

Figure 1B:
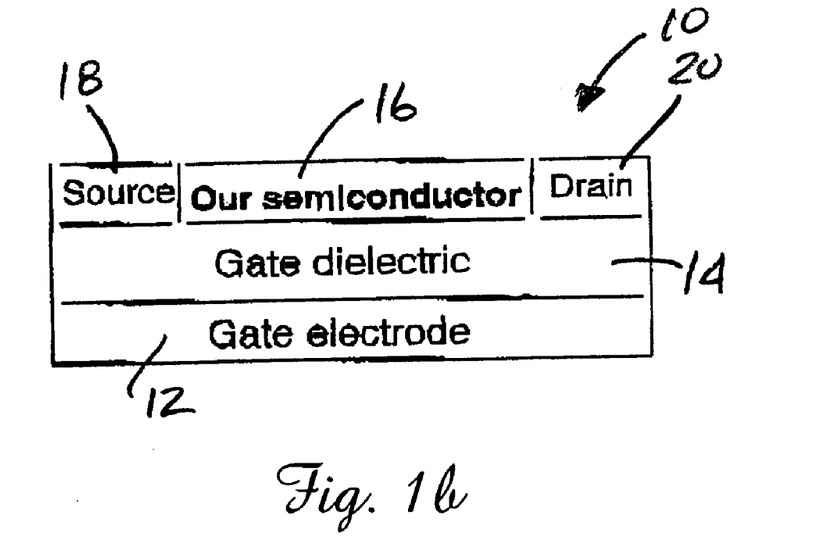

The FET illustrated in FIG. 1a is known as a top-contact configuration. An alternative embodiment of the FET 10 of the present invention is illustrated in FIG. 1b. This configuration is known as a bottom-contact configuration. The gate electrode 12, source electrode 18 and drain electrode 20 may again be any sort of conductor: gold, silver, aluminum, platinum, heavily-doped silicon or an organic conducting polymer. The insulator or gate dielectric 14 can be an oxide such as aluminum oxide or silicone oxide or an insulating polymer such as poly(methylmethacrylate). In either configuration the compound of the present invention may be applied either by solution or vapor methods to form the semiconductor 16.

EXAMPLE 4

The substrate for the field-effect transistors consisted of a heavily-doped Si wafer with thermally grown oxide layer (370 nm), serving as gate electrode and dielectric. Gold source and drain contacts were evaporated to yield devices with channel length of 22 μm and channel width of 340 μm. The gold electrodes were then treated with pentafluorobenzenethiol to improve the electrode interface. A 1-2 wt % solution of the triethylsilyl anthradithiophene derivative of Example 1 in toluene was spread across the device surface using a plastic blade, and the solvent allowed to evaporate. The devices were then heated in air at 90° C. for two minutes to drive off residual solvent.

The triethylsilyl anthradithiophene derivative of Example 1 formed a uniform film of excellent quality yielding hole mobility of 1.0 cm$^2$/Vs with excellent on/off current ratio (10$^7$). The performance of this material is likely due to the close π-stacked interactions in the crystal. The triethylsilyl anthradithiophene derivative adopts a 2-D π-stacking arrangement with a π-face separation of approximately 3.25 Å. The triethylsilyl anthradithiophene derivative was also characterized by a π-overlap of 1.57 Å$^2$ and a lateral slip of 2.75, 1.76 Å. All measurements were performed in air at room temperature and the mobility was calculated from the saturation currents.

Figure 2A:
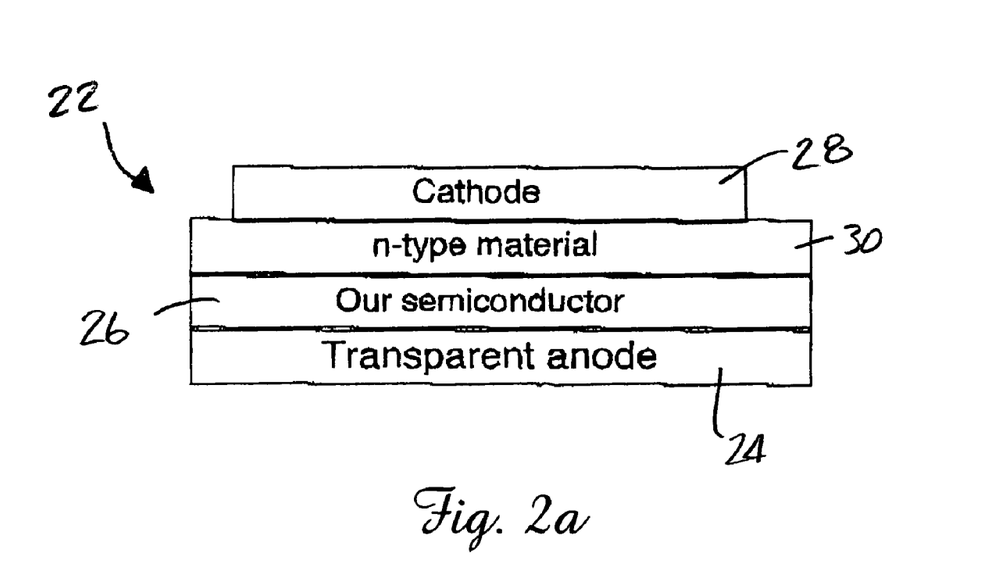
FIGS. 2a and 2b are schematical representations illustrating two possible embodiments of the photovoltaic apparatus of the present invention.

A photovoltaic apparatus 22 is illustrated in FIG. 2a. The photovoltaic apparatus 22 comprises a transparent conductive electrode or anode 24, a semiconductor 26 in the form of a thin layer or film of the compound of the present invention and a bottom electrode or cathode 28.

In the photovoltaic apparatus embodiment illustrated in FIG. 2a, a layer 30 of n-type material is provided between the semiconductor 26 and the cathode 28. In the photovoltaic apparatus 22 illustrated in FIG. 2b the semiconductor 26 comprises the compound of the present invention blended with an n-type material.

In the case of organic solar cells, the compounds of the present invention are typically used as the hole transporter (the "p-type" material). This material must be used in conjunction with an n-type material, defined as any electron-accepting compound (examples: C60 or solubilized derivatives PTCBI, other perylene diimides).

Figure 2B:
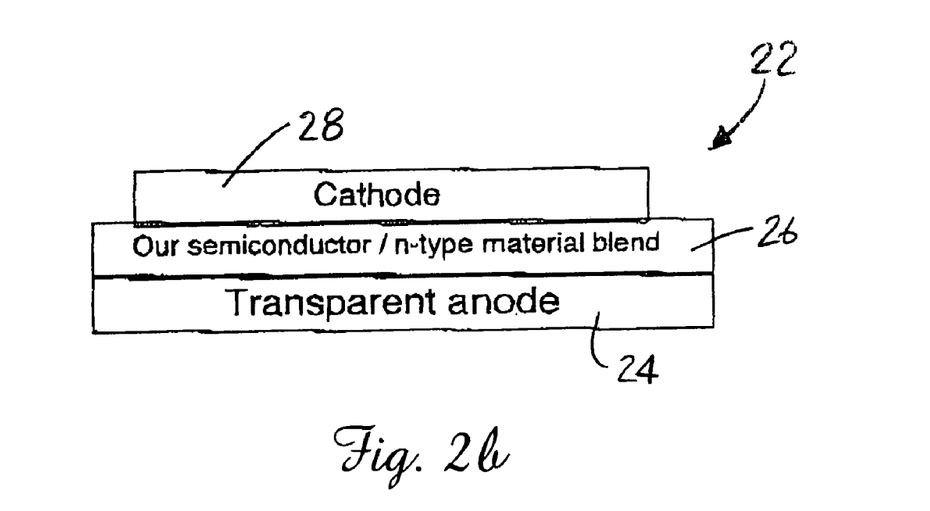

The photovoltaic apparatus 22 can typically be constructed in the two ways illustrated in FIGS. 2a and 2b. As illustrated in FIG. 2a, the p-type compound and the n-type compound are both deposited from vapor or solution in sequential steps, leading to a single heterojunction interface. Alternatively, as illustrated in FIG. 2b, the p-type material and the n-type material may be mixed and deposited from solution on the anode prior to deposition of the cathode material. In this embodiment the p-type and n-type materials phase segregate, leading to multiple heterojunctions in the bulk. In both cases the anode material typically has a high work function and is transparent (ITO or 10 oxide on glass or plastic). In contrast, the cathode 28 is a low work function conductor, and is typically reflective to improve efficiency (aluminum, silver or an indium-gallium eutectic). In either case the anode layer can be pre-coated with a commercial conducting polymer PEDOT in order to improve charge injection efficiency.

What is claimed is:

1. A compound of the formula:

wherein R=an alkyl, perfluoroalkyl, aryl, alkoxy, or triakylsilyl, R'=halogen and X=—O, —S, —Se, or —NH.

2. A compound of the formula:

wherein R=an alkyl, perfluoroalkyl, aryl, alkoxy, or triakylsilyl, R'=hydrogen, alkyl, aryl, perfluoroalkyl, alkoxy, halogen and X=—O, —S, —Se, or —NH.

3. A compound, comprising: a mixture of stereoisomers of the following formulae:

(A₁)

(A₂)

wherein R=an alkyl, perfluoroalkyl, aryl, alkoxy, or triakylsilyl, R'=halogen and X=—O, —S, —Se, or —NH.

4. A compound of the formula:

(A₁)

wherein R=an alkyl, perfluoroalkyl, aryl, alkoxy or trialkylsilyl, R¹=halogen and X=—O, —S, —Se or —NH.

5. A compound of the formula:

(A₂)

wherein R=an alkyl, perfluoroalkyl, aryl, alkoxy or trialkylsilyl, R¹=halogen and X=—O, —S, —Se or —NH.

6. A compound, comprising: a mixture of stereoisomers of the following formulae:

(B₁)

and

(B₂)

wherein R=an alkyl, perfluoroalkyl, aryl, alkoxy, or triakylsilyl, R'=hydrogen, alkyl, aryl, perfluoroalkyl alkoxy, halogen and X=—O, —S, —Se, or —NH.

7. A compound, comprising: a mixture of stereoisomers of the following formulae:

(C₁)

(C₂)

wherein R=an alkyl, perfluoroalkyl, aryl, alkoxy, or triakylsilyl, R'=hydrogen, alkyl, aryl, perfluoroalkyl, alkoxy, halogen and X=—O, —S, —Se, or —NH.

8. A transistor, comprising:

a gate electrode;

a semiconductor constructed from at least one material selected from a group consisting of (A₁)

(A₂)

wherein R=an alkyl, perfluoroalkyl, aryl, alkoxy, or triakylsilyl, R'=halogen and X=—O, —S, —Se, or —NH;

an insulator between said gate electrode and said semiconductor;

a source electrode; and a drain electrode.

9. A transistor, comprising:

a gate electrode;

a semiconductor constructed from at least one material selected from a group consisting of (B₁)

(B₂)

wherein R=an alkyl, perfluoroalkyl, aryl, alkoxy, or triakylsilyl, R'=hydrogen, alkyl, aryl, perfluoroalkyl, alkoxy, halogen and X=—O, —S, —Se, or —NH;

an insulator between said gate electrode and said semiconductor;

a source electrode; and a drain electrode.

10. A transistor, comprising:

a gate electrode;

a semiconductor constructed from at least one material selected from a group consisting of (C₁)

(C₂)

wherein R=an alkyl, perfluoroalkyl, aryl, alkoxy, or triakylsilyl, R'=hydrogen, alkyl, aryl, perfluoroalkyl, alkoxy, halogen and X=—O, —S, —Se, or —NH;
   an insulator between said gate electrode and said semiconductor;
   a source electrode; and
   a drain electrode.

11. A photovoltaic apparatus, comprising:
   a transparent anode;
   a semiconductor constructed from at least one material selected from a group consisting of (B₁)

(B₂)

(C₁)

(C₂)

wherein R=an alkyl, perfluoroalkyl, aryl, alkoxy, or triakylsilyl, R'=hydrogen, alkyl, aryl, perfluoroalkyl, alkoxy, halogen and X=—O, —S, —Se, or —NH;
   an n-type material; and
   a cathode.

12. A photovoltaic apparatus, comprising:
   a transparent anode;
   a semiconductor constructed from at least one material selected from a group consisting of (A₁)

(A₂)

wherein R=an alkyl, perfluoroalkyl, aryl, alkoxy, or triakylsilyl, R'=halogen and X=—O, —S, —Se, or —NH;
an n-type material; and
a cathode.

13. A photovoltaic apparatus, comprising:
a transparent anode;
a semiconductor constructed from a group consisting of

(B₁)

(B₂)

wherein R=an alkyl, perfluoroalkyl, aryl, alkoxy, or triakylsilyl, R'=hydrogen, alkyl, aryl, perfluoroalkyl, alkoxy, halogen and X=—O, —S, —Se, or —NH;
an n-type material; and
a cathode.

14. A photovoltaic apparatus, comprising:
a transparent anode;
a semiconductor constructed from at least one material selected from a group consisting of (C₁)

(C₂)

wherein R=an alkyl, perfluoroalkyl, aryl, alkoxy, or triakylsilyl, R'=hydrogen, alkyl, aryl, perfluoroalkyl, alkoxy, halogen and X=—O, —S, —Se, or —NH;
an n-type material; and
a cathode.

* * * * *